(12) United States Patent
Westbrook (10) Patent No.: US 10,683,339 B2
(45) Date of Patent: Jun. 16, 2020

(54) P75NTR BINDING PROTEIN-FC FUSION PROTEIN AND METHODS OF TREATING PAIN (71) Applicant: Levicept Limited, Sandwich Kent (GB)

(72) Inventor: Simon Westbrook, Sandwich Kent (GB)

(73) Assignee: Levicept Limited, Sandwich Kent (GB)

( * ) Notice: Subject to any disclaimer, the term of this patent is extended or adjusted under 35 U.S.C. 154(b) by 0 days.

(21) Appl. No.: 15/559,368

(22) PCT Filed: Mar. 18, 2016

(86) PCT No.: PCT/EP2016/056049
§ 371 (c)(1),
(2) Date: Sep. 18, 2017

(87) PCT Pub. No.: WO2016/146841
PCT Pub. Date: Sep. 22, 2016

(65) Prior Publication Data
US 2018/0170995 A1    Jun. 21, 2018

(30) Foreign Application Priority Data
Mar. 19, 2015 (GB) .................................. 1504691.5

(51) Int. Cl.
*C07K 14/00* (2006.01)
*A61K 38/00* (2006.01)
*C07K 14/475* (2006.01)
*C07K 14/48* (2006.01)
*A61K 38/18* (2006.01)
*A61K 38/17* (2006.01)
*C07K 14/47* (2006.01)
*A61K 39/395* (2006.01)
*A61K 39/00* (2006.01)
*G01N 33/53* (2006.01)
*C07K 14/705* (2006.01)
*A61P 29/00* (2006.01)
*C07K 16/28* (2006.01)
*C07K 16/46* (2006.01)
*C07K 19/00* (2006.01)
*A61K 38/16* (2006.01)

(52) U.S. Cl.
CPC ...... *C07K 14/70578* (2013.01); *A61K 38/177* (2013.01); *A61K 39/395* (2013.01); *A61P 29/00* (2018.01); *A61K 38/00* (2013.01); *A61K 38/16* (2013.01); *A61K 38/18* (2013.01); *A61K 38/185* (2013.01); *C07K 14/00* (2013.01); *C07K 14/475* (2013.01); *C07K 14/48* (2013.01); *C07K 16/28* (2013.01); *C07K 16/2863* (2013.01); *C07K 16/2878* (2013.01); *C07K 16/46* (2013.01); *C07K 16/461* (2013.01); *C07K 16/462* (2013.01); *C07K 19/00* (2013.01); *C07K 2319/00* (2013.01); *C07K 2319/30* (2013.01); *G01N 2800/28* (2013.01); *G01N 2800/2842* (2013.01)

(58) Field of Classification Search
CPC .............. A61K 39/395; A61K 2300/00; A61K 2039/505; A61K 38/17; A61K 38/00; C07K 2319/30; C07K 2319/00; C07K 14/001; C07K 14/70578; C07K 2319/50; C07K 2317/569; C07K 2317/52; C07K 2317/56; C07K 2317/622; C07K 16/2803; C07K 16/2896; C07K 2317/21; C07K 2317/34; C07K 2317/41; C07K 2317/50; C07K 2317/53; C07K 2317/565; C07K 2317/73; C07K 2317/92; C07K 2317/94; C07K 2319/02; C07K 2319/33
See application file for complete search history.

(56) References Cited

U.S. PATENT DOCUMENTS

| | | | |
|---|---|---|---|
| 8,669,350 | B2 | 3/2014 | Chou |
| 9,764,000 | B2 | 9/2017 | Westbrook |
| 9,873,728 | B2 | 1/2018 | Westbrook |
| 2007/0243132 | A1 | 10/2007 | Russell-Jones |
| 2008/0182978 | A1 | 7/2008 | Rosenthal |
| 2009/0232808 | A1 | 9/2009 | Priest |
| 2010/0061981 | A1 | 3/2010 | O Leary |
| 2011/0014208 | A1 | 1/2011 | Macdonald |
| 2013/0164286 | A1 | 6/2013 | Chou |
| 2014/0017235 | A1 | 1/2014 | Rosenthal |
| 2017/0204156 | A1 | 7/2017 | Westbrook |
| 2018/0161392 | A1 | 6/2018 | Westbrook |

(Continued)

FOREIGN PATENT DOCUMENTS

| | | | | |
|---|---|---|---|---|
| CN | 102233128 | | 11/2011 | |
| CN | 102586313 | | 7/2012 | |
| CN | 102233128 B | * | 4/2013 | ............. A61K 38/17 |

(Continued)

OTHER PUBLICATIONS

'T Hart et al. Curr. Opin. Neurol. 2003. 16: 375-383.*

(Continued)

*Primary Examiner* — Chang-Yu Wang (74) *Attorney, Agent, or Firm* — Dennis A. Bennett; Stephanie M. Greer; Chris Marion (57) ABSTRACT

The present invention relates to a new p75NTR neurotrophin binding protein (NBP)-Fc fusion protein comprising a p75NTR (NBP) portion and an immunoglobulin portion. In certain embodiments, the p75NTR (NBP)-Fc fusion protein is for use in the treatment of pain and/or a symptom of pain.

7 Claims, 1 Drawing Sheet

Specification includes a Sequence Listing.

(56) References Cited

U.S. PATENT DOCUMENTS

2018/0273603 A1  9/2018  Westbrook

FOREIGN PATENT DOCUMENTS

| | | |
|---|---|---|
| OA | 2012101664 | 8/2012 |
| WO | 1992007076 | 4/1992 |
| WO | 2005037867 | 7/2005 |
| WO | 2006079176 | 8/2006 |
| WO | 2007026567 | 3/2007 |
| WO | 2013136078 A1 | 9/2013 |
| WO | 2015040398 | 3/2015 |
| WO | 2016009222 | 1/2016 |
| WO | 2016146841 | 9/2016 |

OTHER PUBLICATIONS

CN102233128B—English version published on Nov. 9, 2011.*
Wang, Yong-Tang et al., "Ameliorative Effects of p75NTR-ED-Fc on Axonal Regeneration and Functional Recovery in Spinal Cord-Injured Rats," Molecular Neurobiology, Humana Press, US, 52(3):1821-34, (Nov. 15, 2014).
Barthel, C. et al., "Nerve Growth Factor and Receptor Expression in Rheumatoid Arthritis and Spondyloarthritis", Arthritis Res Ther., 11(3):R82, (2009).
Chu, C. et al., "Mitochondrial Dependence of Nerve Growth Factor-Induced Mechanical Hyperalgesia", Pain, 152 (8):1832-7, (2011).
Cirillo, G. et al., "Intrathecal NGF Administration Reduces Reactive Astrocytosis and Changes Neurotrophin Receptors Expression Pattern in a Rat Model of Neuropathic Pain", Cell Mol Neurobiol., 30(1):51-62, (2010).
Cowan, W., "Viktor Hamburger and Rita Levi-Montalcini: the Path to the Discovery of Nerve Growth Factor", Annu Rev Neurosci., 24:551-600, (2001).
Fukui, Y. et al., "Low Affinity NGF Receptor (p75 Neurotrophin Receptor) Inhibitory Antibody Reduces Pain Behavior and CGRP Expression in DRG in the Mouse Sciatic Nerve Crush Model", J Orthop Res., 28(3):279-83, (2010).
Ghilardi, J. et al., "Sustained Blockade of Neurotrophin Receptors TrkA, TrkB and TrkC Reduces Non-Malignant Skeletal Pain but Not the Maintenance of Sensory and Sympathetic Nerve Fibers", Bone., 48(2):389-98, (2011).
Hayashi, K. et al., "Involvement of NGF in the Rat Model of Persistent Muscle Pain Associated with Taut Band", J Pain, 12(10):1059-68, (2011).
He, X. et al., "Structure of Nerve Growth Factor Complexed with the Shared Neurotrophin Receptor p75", Science, 304(5672):870-5, (2004).
International Application No. PCT/EP2016/056049; International Preliminary Report on Patentability, dated Sep. 19, 2017; 7 pages.
International Application No. PCT/EP2016/056049; International Search Report and Written Opinion of the International Searching Authority, dated May 23, 2016; 11 pages.
International Application No. PCT/GB2014/052833; International Search Report and Written Opinion of the International Searching Authority, dated Dec. 17, 2014; 9 pages.
Iwakura, N. et al., "Role of Low-Affinity Nerve Growth Factor Receptor Inhibitory Antibody in Reducing Pain Behavior and Calcitonin Gene-Related Peptide Expression in a Rat Model of Wrist Joint Inflammatory Pain", J Hand Surg Am., 35(2):267-73, (2010).
Jung, K. et al., "Regulated Intramembrane Proteolysis of the P75 Neurotrophin Receptor Modulates its Association with the TrkA Receptor", J Biol Chem., 278(43):42161-9, (2003).
Kanning, C. et al., "Proteolytic Processing of the P75 Neurotrophin Receptor and Two Homologs Generates C-terminal Fragments with Signaling Capability", J Neurosci., 23(13):5425-36, (2003).
Kenchappa, R. et al., "P75 Neurotrophin Receptor-Mediated Apoptosis in Sympathetic Neurons Involves a Biphasic Activation of JNK and Up-Regulation of Tumor Necrosis Factor-Alpha-Converting Enzyme/ADAM17", J Biol Chem., 285(26):20358-68, (2010).
MCDonald, C. et al., "Targeting the Nogo Receptor Complex in Diseases of the Central Nervous System", Curr Med Chem., 18(2):234-44, (2011).
Orita, S. et al., "Inhibiting Nerve Growth Factor or its Receptors Downregulates Calcitonin Gene-Related Peptide Expression in Rat Lumbar Dorsal Root Ganglia Innervating Injured Intervertebral Discs", J Orthop Res., 28 (12):1614-20, (2010).
Pezet, S. et al., "Differential Regulation of NGF Receptors in Primary Sensory Neurons by Adjuvant-Induced Arthritis in the Rat", Pain, 90(1-2):113-25, (2001).
Raychaudhuri, S. et al., "Nerve Growth Factor: A key Local Regulator in the Pathogenesis of Inflammatory Arthritis", Arthritis Rheum., 63(11):3243-52, (2011).
Svensson, P. et al., "Human Nerve Growth Factor Sensitizes Masseter Muscle Nociceptors in Female Rats", Pain, 148(3):473-80, (2010).
Truzzi, F. et al., "P75 Neurotrophin Receptor Mediates Apoptosis in Transit-Amplifying Cells and its Overexpression Restores Cell Death in Psoriatic Keratinocytes", Cell Death Differ., 18(6):948-58, (2011).
Ueda, K. et al., "Local Administration of a Synthetic Cell-Penetrating Peptide Antagonizing TrkA Function Suppresses Inflammatory Pain in Rats", J Pharmacol Sci., 112(4):438-43, (2010).
Watanabe, T. et al., "The P75 Receptor is Associated with Inflammatory Thermal Hypersensitivity", J Neurosci Res., 86(16):3566-74, (2008).
Yamaoka, J. et al., "Changes in cutaneous sensory nerve fibers induced by skin-scratching in mice", J Dermatol Sci., 46(1):41-51, (2007).
Amet, N. et al., "Insertion of the Designed Helical Linker Led to Increased Expression of tf-Based Fusion Proteins", Pharm Res., 26(3):523-8, (2009).
Armour, K. et al., "Recombinant human IgG molecules lacking Fcgamma receptor I binding and monocyte triggering activities", Eur J Immunol., 29(8):2613-24, (1999).
Bai, Y. et al., "Recombinant Granulocyte Colony-Stimulating Factor-Transferrin Fusion Protein as an Oral Myelopoietic Agent", Proc Natl Acad Sci., 102(20):7292-6, (2005).
Bothwell, M. et al., "Dissociation Equilibrium Constant of Beta Nerve Growth Factor", J Biol Chem., 252(23):8532-6, (1977).
Bowie, J. et al., "Deciphering the Message in Protein Sequences: Tolerance to Amino Acid Substitutions", Science, 247(4948):1306-10, (1990).
Burgess, W. et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J Cell Bio., 111:2129-38, (1990).
Cell Signaling Technology, p75NTR Antibody #2693 (2010).
Dray, A. et al., "Arthritis and Pain. Future Targets to Control Osteoarthritis Pain", Arthritis Research & Ther., 9(3):pp. 1-14, (2007).
EPO Preliminary Response and Claims Amendment, PCT/GB2014/052833, dated Jul. 20, 2015.
Fukui, Y. et al., "Low Affinity NCF Receptor (p75 Neurotrophin Receptor) Inhabitory Antibody Reduces Pain Behavior and CGRP Expression in DRG in the Mouse Sciatic Nerve Crush Model", J Orthop Res., 28(3):279-83, (2010).
Guo, J. et al., "proNGF inhibits proliferation and oligodendrogenesis of postnatal hippocampal neural stem/ progenitor cells through p 75NTR in vitro", Stem Cell Research, 11(2):874-87, (2013).
Harding, F. et al., "The Immunogenicity of Humanized and Fully Human Antibodies: Residual Immunogenicity Resides in the CDR Regions", MAbs, 2(3):256-65, (2010).
Huang, E. et al., "Trk Receptors: Roles in Neuronal Signal Transduction", Annu Rev Biochem., 72:609-42, (2003).
Ichim, G. et al., "Neurotrophins and Cell Death", Exp Cell Res., 318(11):1221-8, (2012).
International Application No. PCT/GB2013/050632; International Preliminary Report on Patentability, dated Sep. 16, 2014; 9 pages.

(56) References Cited

OTHER PUBLICATIONS

International Application No. PCT/GB2013/050632; International Search Report and Written Opinion of the International Searching Authority, dated Jun. 6, 2013; 13 pages.
International Application No. PCT/GB2014/052833; International Preliminary Report on Patentability, dated Sep. 18, 2015; 9 pages.
International Application No. PCT/GB2015/052083; International Preliminary Report on Patentability, dated Jan. 17, 2017; 9 pages.
International Application No. PCT/GB2015/052083; International Search Report and Written Opinion of the International Searching Authority, dated Jan. 10, 2015; 13 pages.
Johnson, D. et al., "Expression and Structure of the Human NGF Receptor", Cell., 47(4):545-54, (1986).
Lane, N. et al., "RN624 (Anti-NGF) Improves Pain and Function in Subjects with Moderate Knee Osteoarthritis: A Hhase I Study", Arthritis & Rheumatism, 52(9 Suppl.):S461, 3 pages, (2005).
Marler, K. et al., "Pro-Neurotrophins Secreted From Retinal Ganglion Cell Axons and Necessary for EphrinA-p75—Mediated Axon Guidance", Neur Dev., 5(30):10 pages, (2010).
Ngo, J. et al., "Computational Complexity, Protein Structure Prediction and Levinthal Paradox", In Mers and Le Grand (Eds.) The Protein Folding Problem and Tertiary Structure Prediction, pp. 491-495, (1994).
Pawson, T. et al. "Assembly of Cell Regulatory Systems Through Protein Interaction Domains", Science, 300:445-52, (2003).
Pincheira, R. et al., "The Sall2 Transcription Factor is a Novel p75NTR Binding Protein that Promotes the Development and Functipn of Neurons", Ann. N Y Acad Sci., 1144:53-5, (2008).
Rabizadeh, S. et al., "Induction of Apoptosis by the Low-Affinity NGF Receptor", Science, 261(5119):345-8, (1993).
Radeke, M. et al., "Gene Transfer and Molecular Cloning of the Rat Nerve Growth Factor Receptor", Nature, 325(6105):593-7, (1987).
Stas, P. et al., "Immunogenicity Assessment of Antibody Therapeutics", Recombinant Antibodies for Immunotherapy, Ch. 2:20-43, (2009).
Tria, M. et al., "Pharmacokinetics of Nerve Growth Factor (NGF) Following Different Routes of Administration to Adult Rats", Exp Neurol., 127(2):178-83, (1994).
U.S. Appl. No. 14/384,302; Examiner-Initiated Interview Summary, dated May 18, 2017; 1 page.
U.S. Appl. No. 14/384,302; Notice of Allowance, dated May 18, 2017; 9 pages.
U.S. Appl. No. 15/022,505; Examiner-Initiated Interview Summary, dated Sep. 15, 2017; 1 page.
U.S. Appl. No. 15/022,505; Non-Final Office Action, dated Jan. 30, 2017; 37 pages.
U.S. Appl. No. 15/022,505; Notice of Allowance, dated Sep. 15, 2017; 10 pages.
U.S. Appl. No. 15/326,936; Non-Final Office Action, dated Dec. 5, 2018; 17 pages.
U.S. Appl. No. 15/680,872; Final Office Action, dated Oct. 18, 2019; 7 pages.
U.S. Appl. No. 15/680,872; Non-Final Office Action, dated Mar. 19, 2019; 17 pages.
U.S. Appl. No. 15/844,022; Non-Final Office Action, dated Dec. 14, 2018; 32 pages.
Vilar, M. et al., "Activation of the p 75 neurotrophin receptor through conformational rearrangement of disulphide-linked eceptor dimers", Neuron., 62(1):72-83, (2009).
Vilar, M. et al., "Ligand-Independent Signaling by Disulfide-Crosslinked Dimers of the p75 Neurotrophin Receptor", J Cell Sci., 122(Pt 18):3351-7, (2009).
Wells, J. "Additivity of Mutational Effects in Proteins", Biochemistry., 29(37):8509-8517, (1990).
Zampieri, N. et al. "Cleavage of p75 Neurotrophin Receptor by Alpha-Secretase and Gamma-Secretase Requires Specific Receptor Domains", J Biol Chem., 280(15):14563-71, (2005).
Zhao, H. et al., "Increasing the Homogeneity, Stability and Activity of Human Serum Albumin and Interferon-Alpha2b Fusion Protein by Linker Engineering", Protein Expr Purif., 61(1):73-7, (2008).

* cited by examiner

P75NTR BINDING PROTEIN-FC FUSION PROTEIN AND METHODS OF TREATING PAIN

CROSS REFERENCE TO RELATED APPLICATIONS

This application is a U.S. national stage filing under 35 U.S.C. § 371 of PCT International Application No. PCT/EP2016/056049, filed Mar. 18, 2016, which claims the benefit of priority to Great Britain Application No. 1504691.5, filed Mar. 19, 2015. Each of the above-referenced applications is expressly incorporated by reference in its entirety.

FIELD OF INVENTION

The present invention relates to an improved p75NTR neurotrophin binding protein (NBP)-Fc fusion protein comprising a p75NTR(NBP) portion and an immunoglobulin portion. In certain embodiments, the p75NTR(NBP)-Fc fusion protein is for use in the treatment of pain.

BACKGROUND TO THE INVENTION

It has been documented that NGF and other neurotrophins (BDNF, NT-3 and NT-4/5) play a significant role in pathology for example pain due to osteoarthritis, pancreatitis, rheumatoid arthritis, psoriasis, pruritis and multiple sclerosis (Watanabe et al., 2008 J Neurosci Res. 86(16):3566-74; Raychaudhuri et al., 2011 Arthritis Rheum. 63(11):3243-52; Barthel et al., 2009 Arthritis Res Ther. 11(3):R82; Truzzi et al., 2011 Cell Death Differ. 18:948-58; McDonald et al., 2011 Curr Med Chem. 18:234-44; Yamaoka et al., 2007 J Dermatol Sci. 46(1):41-51). It has been demonstrated that selective antibodies to any of the neutrophins; either NGF or BDNF, NT-3 and NT-4/5 significantly reduce pain. Furthermore, antibodies directed to the neurotrophin receptors p75NTR Trk A, Trk B or Trk C have also been demonstrated to be efficacious in models of pain (Orita S et al., 2010 J Orthop Res. 28:1614-20; Svensson P et al., 2010 Pain. 148:473-80; Iwakura et al., 2010 J Hand Surg Am. 35:267-73; Cirilio et al., 2010 Cell Mol Neurobiol. 30:51-62; Pezet et al., 2010 Pain. 90:113-25; Hayashi et al., 2011 J Pain. 12:1059-68; Chu et al., 2011 Pain. 152:1832-7; Ueda et al., 2010 J Pharmacol Sci.; 112:438-43; Ghilardi et al., 2010 Bone. 48:389-98; Fukui et al., 2010 J Orthop Res. 2010; 28:279-83). Fukui et al., (2010) in a model of pain (mechanical allodynia following sciatic nerve crush) demonstrated significant efficacy on pain related endpoints following treatment with an anti-p75NTR antibody. It was concluded from this study that the treatment with a p75NTR inhibitory antibody reduced CGRP and p75NTR expression resulting in a significant reduction in pain.

The p75 neutrophic receptor (p75NTR) is a member of the tumor necrosis factor receptor superfamily (TNFR-SF) known to bind to neurotrophic growth factor (NGF), brain-derived neurotrophic factor (BDNF), neurotrophin 3 (NT-3), and neurotrophin 4/5 (NT-4/5). p75NTR undergoes sequential proteolytic cleavage by α-secretase and γ-secretase activities and matrix metalloproteinases (MMPs), releasing its intracellular domain (ICD) into the cytoplasm, in a manner analogous to the cleavage-dependent signaling pathway of Notch and β-amyloid precursor protein (Jung et al., 2003 J Biol Chem 278:42161-42169; Kanning et al., 2003 J Neuro-sci 23:5425-5436). Cytoplasmic release of the p75NTR ICD by this pathway promotes signaling by associated NRIF (Kenchappa et al., 2006 Neuron 50:219-232).

The role of the extracellular domain of p75NTR, following the proteolytic cleavage by α-secretase and γ-secretase activities and MMPs is not fully understood. However this molecule has been shown by the present applicants to be useful in the treatment of pain (WO2013/136078). The protein has also been advantageously coupled to Fc antibody fragments in the form of a fusion protein by the present applicants (PCT/GB2014/052833).

The present application relates to an improved p75NTR-Fc fusion protein.

SUMMARY OF INVENTION

In a first aspect the present invention relates to a p75NTR neurotrophin binding protein (NBP)-Fc fusion protein, comprising or consisting of the amino acid sequence set forth SEQ ID NO. 1.

Preferably the p75NTR(NBP) binds to any of NGF, BDNF, NT3 or NT4/5 with a binding affinity ($K_d$) of between about 1 pM to about 100 nM as measured by surface plasmon resonance at 20° C.

The present invention also relates to a p75NTR neurotrophin binding protein(NBP)-Fc fusion protein, comprising or consisting of the amino acid sequence set forth in SEQ ID NO. 1 for use in therapy. In a further aspect the present invention relates to a p75NTR neurotrophin binding protein (NBP)-Fc fusion protein, comprising or consisting of the amino acid sequence set forth in SEQ ID NO. 1 for use in the treatment of pain.

Also provided herein is a nucleic acid molecule encoding the p75NTR(NBP)-Fc fusion protein according to the first aspect of the invention, optionally further comprising a signal sequence. This nucleic acid may be included in a replicable expression vector for transfecting a cell, optionally a mammalian cell. Preferably the vector is a viral vector. In a further embodiment a host cell harbouring the nucleic acid molecule described above is provided.

In addition, there is provided herein the nucleic acid molecule described above, for use in therapy, more specifically for use in the treatment of pain.

In yet a further aspect of the invention there is provided a pharmaceutical composition comprising a p75NTR neurotrophin binding protein(NBP)-Fc fusion protein, comprising or consisting of the amino acid sequence set forth in SEQ ID NO. 1 and a pharmaceutically acceptable diluent or carrier.

Preferably the pharmaceutical composition further comprises one or more additional pharmaceutically active components. Also provided herein is a method of treating and or preventing pain in an individual comprising administering to said individual a therapeutically effective amount of the p75NTR(NBP)-Fc fusion protein of SEQ ID NO. 1, optionally further comprising a pharmaceutically acceptable carrier.

DETAILED DESCRIPTION OF THE INVENTION

Glycosylation of proteins is a very common biological process which has a variety of effects. Both naturally occurring and recombinant proteins may undergo glycosylation, though in the case of recombinant proteins, which may not be expressed in their native cell, glycosylation patterns can vary significantly from the native pattern. Differences in glycosylation of a recombinant product can lead to differences in activity, half-life and stability when compared to the native product.

Furthermore, highly glycosylated proteins are a challenge to manufacture for clinical use due to potential variability in the sugars added during post-translation modification. Ensuring that the glycosylated molecule does not change between batches is an additional difficulty. Although proteins may be engineered to reduce the likelihood of unfavourable glycosylation, identifying the position and nature of the glycosylation is problematic when there are many potential sites. More importantly, even minor protein engineering carries with it the risk that activity will be adversely affected. Control of glycosylation in therapeutic proteins while maintaining acceptable activity therefore represents a particular challenge.

The p75 neurotrophin receptor p75NTR in its native form exists as a transmembrane glycoprotein. Family members are characterised by multiple cysteine-rich domains for ligand binding, a single transmembrane sequence extracellular domain (ECD), and a non-catalytic cytoplasmic domain. Endogenous soluble ECD of p75NTR is produced by regulated intramembrane proteolysis by α-secretase that cleaves the protein near the membrane junction of the ECD. This is followed by γ-secretase cleavage in the middle of the transmembrane domain resulting in the release of the cytoplasmic domain.

Figure 1:
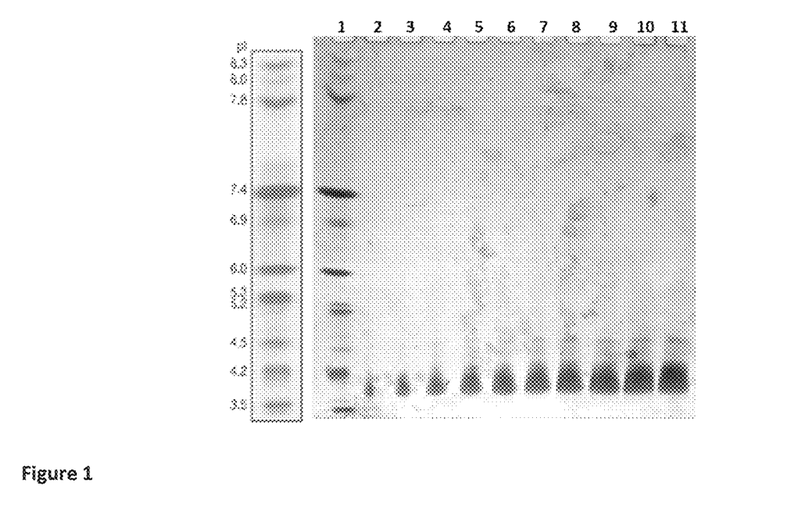
FIG. 1: IEF chromatogram of purified p75NTR-Fc (SEQ ID NO. 3) from pooled cells demonstrating indistinct protein bands. 1: Novex pH 3-10 Marker; 2: p75NTR-Fc, 1 µg; 3: p75NTR-Fc, 2 µg; 4: p75NTR-Fc, 4 µg; 5: p75NTR-Fc, 6 µg; 6: p75NTR-Fc, 8 µg; 7: p75NTR-Fc, 10 µg; 8: p75NTR-Fc, 12 µg; 9: p75NTR-Fc, 15 µg; 10: p75NTR-Fc, 18 µg; 11: p75NTR-Fc, 20 µg.

The present inventors have observed that the structure of the ECD of p75NTR consists of a stalk region (SEQ ID NO. 4) that is prone to glycosylation. As shown in FIG. 1, this glycosylation results in the p75NTR(NBP)-Fc fusion protein having a number of indistinct bands on an IEF gel ranging from 3.4-4.2 (significantly lower than the theoretical iso-electric point of the protein of 4.5). This property of the molecule provides a number of disadvantages ranging from manufacture, formulation, identification of the molecule, batch to batch variation, immunogenicity, pharmacokinetics and possible pharmacology.

Figure 2:
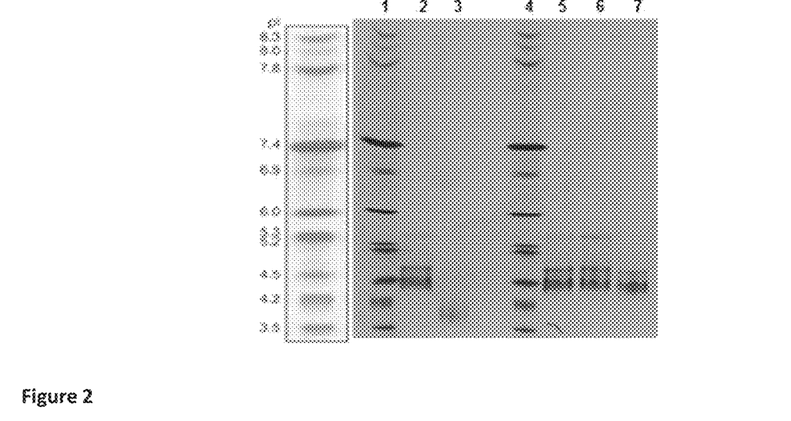
FIG. 2: IEF gel of truncated p75NTR-Fc (SEQ ID NO. 1) demonstrating distinct protein bands at the iso-electric point of the protein. 1: IEF pH 3-10 markers (5 μL); 2: Truncated p75NTR-Fc, Run 1; 3: p75NTR-Fc; 4: IEF pH 3-10 markers (5 μL); 5: Truncated p75NTR-Fc, Run 1; 6: Truncated p75NTR-Fc, Run 2; 7: Truncated p75NTR-Fc, Run 3.

A truncated form of the p75NTR(NBP)-Fc fusion in which this stalk region has been removed (referred to herein as Truncated p75NTR(NBP)-Fc; (SEQ ID NO. 1) has a theoretical iso-electric point of 4.6. As demonstrated in FIG. 2 the observed iso-electric point of this molecule is very similar to that of the theoretical iso-electric point. Thus, Truncated p75NTR(NBP)-Fc has a superior manufacturability profile, improved protein identification, greater range possible formulations, reduced immunogenicity potential and improved pharmacokinetic profile.

Surprisingly, despite this significant change to the structure of the molecule, truncated p75NTR(NBP)-Fc still hinds the four neurotrophins (BDNF, BGF, NT-3 and NT-4/5) with comparable affinity to the non-truncated molecule. Furthermore, the present inventors have demonstrated that the truncated molecule successfully inhibits neurotrophin signalling via the Trk family receptors in an in vitro cellular model assay. This confirms the utility of this molecule in therapy, particularly in treatments of neurotrophin-related conditions such as pain.

The highly glycosylated p75NTR-Fc has significant immunogenic potential: variation in glycosylation pattern and/or differences to the endogenous soluble form of p75NTR may lead to the production of anti-drug antibodies (ADA). Thus the sparsely-glycosylated, truncated form of p75NTR-Fc (SEQ ID NO. 1) has a reduced potential for stimulating the production of ADAs. Variations in glycosylation pattern are less likely between different batches and between the exogenous and endogenous p75NTR.

Glycosylation of proteins may be associated with longer half-life. The addition of the Fc domain of IgG1 ensures that SEQ ID NO. 1 has a suitable pharmacokinetic profile for clinical use. However, the time to maximum plasma concentrations following subcutaneous injection of the highly glycosylated form of p75NTR-Fc is approximately 4-6 days. Highly glycosylated molecules may bind to mucin leading to a slower absorption rate. Consequently, the rate of on-set is slower compared with the absorption rate of molecules with less glycosylation. Removing the glycosylation and forming the truncated p75NTR-Fc molecule (SEQ ID NO. 1) reduces mucin binding, thereby increasing the rate of absorption and increasing onset of efficacy following subcutaneous injections.

The p75NTR(NBP)-Fc fusion protein of the present invention preferably binds to any one or more of NGF, BDNF, NT3 or NT4/5 with a binding affinity ($K_d$) of between about 1 pM to about 100 nM. In some preferred embodiments, the binding affinity ($K_d$) is between about 5 pM and any of about 10 pM, 20 pM, 40 pM, 50 pM 100 pM, 0.2 nM, 0.5 nM, 1.0 nM 1.5 nM 2 nM, 2.5 nM, 3 nM, 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM, 15 nM, 20 nM, 25 nM, 30 nM, 35 nM, 40 nM, 45 nM, 50 nM or 100 nM as measured in an in vitro binding assay for NGF, BDNF, NT3 or NT4/5 such as described herein preferably as measured by surface plasmon resonance at 20° C. In some further preferred embodiments, binding affinity ($K_d$) is or is less than any of about 10 pM, 20 pM, 40 pM, 80 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 950 pM or 1 nM as measured in an in vitro binding assay for p75NTR(NBP)-Fc fusion protein with the neurotrophins such as described herein, preferably as measured by surface plasmon resonance at 20° C. In a further more preferred embodiment the binding affinity ($K_d$) is about 10 pM, 0.3 nM or about 1 nM, as measured in an in vitro binding assay for p75NTR(NBP)-Fc fusion protein with the neurotrophins such as described herein, preferably as measured by surface plasmon resonance at 20° C.

Preferably the p75NTR(NBP)-Fc fusion protein of the invention is for use in the treatment of pain. Without wishing to be bound by any particular theory, the inventors believe that the p75NTR(NBP)-Fc fusion protein achieves efficacy in the treatment of pain or a symptom of pain by effecting the functional activity of the aforementioned neurotrophins, (defined as modulating or up or down regulating the functional activity of the neurotrophins) NGF, BDNF, NT3 or NT4/5, for example the functional activity of the aforementioned neurotrophins resulting from their interaction with their respective receptors.

Preferably the p75NTR(NBP)-Fc fusion protein effects the functional activity of BDNF as assessed by functional assay of any of growth and differentiation of neurons and synapses, survival and differentiation in neuronal cell culture, Trk signalling, stimulation of axon outgrowth in vitro or in vivo.

Preferably the p75NTR(NBP)-Fc fusion protein effects the functional activity of NGF as assessed by measuring NGF binding to and activation of TrkA, as demonstrated in classical neuron survival assays (such as provided in Cowan et al. *Annu. Rev. Neurosci.* 2001; 24:551-600).

Preferably the p75NTR(NBP)-Fc fusion protein effects the functional activity of NT3 as assessed by measuring NT3 binding to and activation of endogenous Trk receptor activity, as demonstrated in Trk receptor phosphorylation, mitogen-activated protein kinase phosphorylation reporter assays or cell survival and neurite extension assays.

Preferably the p75NTR(NBP)-Fc fusion protein effects the functional activity of NT4/5 as assessed by measuring NT4/5 in vitro or in vivo phosphorylation and activation assays for example in myelin basic protein (MBP) phosphorylation assays or alternatively in vivo in a Matrigel angiogenesis assay of vascular endothelial growth factor (VEGF)/basic fibroblast growth factor-induced angiogenesis.

Preferably the p75NTR(NBP)-Fc fusion protein binds to the contact residues of one or more of the neurotrophins NGF, NT3, BDNF and NT4/5 as shown in He and Garcia (2001) Science, 301, pages 870-805.

Preferably the p75NTR(NBP)-Fc fusion protein is soluble, preferably soluble in aqueous solution, preferably soluble in a biological fluid such as scrum, plasma, blood.

According to the present invention, the p75NTR(NBP)-Fc fusion protein demonstrates advantageous biological properties of improved solubility of p75NTR(NBP) and/or stability of p75NTR(NBP) and/or improved serum half life p75NTR(NBP). Improved solubility is desirable in order that bioavailability of the p75NTR(NBP) is maximized on administration and accurate dosage of the p75NTR(NBP) can be determined and carried out. Improved solubility is advantageous to overcome the problem of aggregates which are undesirable causing pain in delivery in-vivo and leading to potential inflammation. Improved serum half life has the advantage of facilitating reduced levels or reduced frequency of dose requirement during use for treatment in order to achieve the equivalent or maintained therapeutic effect of the p75NTR(NBP) delivered. A prolonged half life and higher stability in blood or serum has the advantage of permitting a dosage regime of less frequent dosing and/or lower dosing levels hence reducing potential toxicity or side effects in-vivo. In this case the p75NTR(NBP)-Fc fusion protein is more potent in its therapeutic effect and/or more stable in the circulation. The resulting lower or less frequent doses are advantageous in minimising any potential toxic effects or side effects potentially associated with p75NTR(NBP) administration. Further patient compliance with any dosage regimen is likely to be improved. The molecular weight of the p75NTR(NBP)-Fc fusion protein is also increased over p75NTR(NBP) alone. One of the advantages is that the molecule will be primarily retained in the blood circulation system when administered intravenously. This reduces the risk of penetration to undesired sites for example the central nervous system. It also makes the molecule suitable for retention or concentration in the tissues targeted.

The p75NTR(NBP)-Fc fusion protein can be shown to demonstrate improved solubility of p75NTR(NBP) and/or improved stability of p75NTR(NBP) and/or improved serum half life in comparison to p75NTR(NBP) alone.

Preferably the improved solubility is solubility in an aqueous solution such as water preferably with excipients such as buffers and/or salts at preferably at a physiological pH, preferably at between pH 5 to pH 8, preferably about pH 7, or is solubility in a biological fluid such as serum or blood. Preferably the improved stability is stability of activity or structural integrity of the p75NTR(NBP) protein due to the effects of denaturation, oxidation, fragmentation or aggregation over a period of time, during a period storage or following freeze and thaw. Structural stability can be judged by standard measures of denaturation, oxidation, aggregation or aggregation; stability of activity can be measured by the binding or functional assays disclosed herein, methods of measuring protein serum half life are known.

Preferably the p75NTR(NBP)-Fc fusion protein can be expressed at high levels from variety of mammalian host cells to provide a single species and can be efficiently purified by affinity chromatography for example by binding to *Staphylococcus aureus* protein A. Preferably the p75NTR(NBP)-Fc fusion protein can dimerise and preferably the dimer has increased affinity to neurotrophins NGF, BDNF, NT3 or NT4/5 in comparison to p75NTR(NBP) alone. Tighter binding has the advantage of higher potency and a higher therapeutic efficacy as judged by the p75NTR(NBP) effects for example as determined by neurotrophin functional assays disclosed herein. Higher potency has the benefit that the p75NTR(NBP)-Fc fusion protein can be used at lower dosage amounts to achieve the same therapeutic efficacy hence reducing potential toxicity or side effects in-vivo.

Preferably the p75NTR(NBP)-Fc fusion protein of the invention has a half life in-vivo of about or more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 hours+/−1 hour, further preferably the p75NTR(NBP)-Fc fusion protein of the invention has a half life in-vivo of about or more than 24 hours.

Further preferably the p75NTR(NBP)-Fc fusion protein of the invention has a half life in-vitro of about or more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 days+/−1 day, further preferably the p75NTR(NBP)-Fc fusion protein of the invention has a half life in-vitro of about or more than 6 days. Preferably the stability is measured at about physiological pH, in a buffered aqueous solution, preferably at 20° C. or 37° C.

According to the foregoing preferred embodiments, preferably the in-vivo half life is half life in rat or half life in human, more preferably in human. Preferably the half life is determined from serum measurements of the levels of p75NTR(NBP)-Fc fusion protein of the invention following administration in-vivo for example by intravenous or subcutaneous injection.

According to another aspect of the invention there is provided a nucleic acid molecule encoding the p75NTR (NBP)-Fc fusion protein according to the first or second aspects. Preferably the nucleic acid molecule is for use in the treatment of pain.

According to a preferred embodiment of the present invention the nucleic acid molecule may further comprise a region encoding a signal sequence, preferably a p75NTR signal sequence for example a DNA or RNA sequence. A representative signal or leader sequence is provided herein as SEQ ID NO. 2.

According to another aspect of the invention there is provided a replicable expression vector for transfecting a cell, the vector comprising the nucleic acid molecule described herein, preferably the vector is a viral vector. Preferably the vector is for use in the treatment of pain.

Further according to the above aspects of the invention there is provided a method of expressing the nucleic acid molecule or the vector of the invention to produce or secrete the p75NTR(NBP)-Fc fusion protein. Preferably the method comprises the introduction of the nucleic acid molecule or vector into a cell and expression of the nucleic acid therein to produce or secrete the p75NTR(NBP)-Fc fusion protein. Preferably the nucleic acid molecule or vector is introduced into the cell in-vitro alternatively in-vivo. Preferably the expressed p75NTR(NBP)-Fc fusion protein is expressed in-vitro, optionally further isolated and purified, alternatively preferably the expressed p75NTR(NBP)-Fc fusion protein is expressed in-vivo, preferably the in-vivo expression constitutes gene therapy. Preferably the vector is a replicable expression vector, optionally for transfecting a mammalian cell, preferably the vector is a viral vector. According to another aspect of the invention there is provided a host cell harbouring the nucleic acid molecule or vector as described herein, preferably the cell is a mammalian cell.

A method for expressing the protein is exemplified in the examples.

According to another aspect of the invention there is provided the p75NTR(NBP)-Fc fusion protein for use in the treatment of pain, or a nucleic acid or vector for use in the treatment of pain. Pain may include but is not limited to:

(a) acute pain and/or spontaneous pain,
(b) chronic pain and/or on-going pain,
(c) inflammatory pain including any one of arthritic pain, pain resulting from osteoarthritis or rheumatoid arthritis, resulting from inflammatory bowel diseases, psoriasis and eczema
(d) nociceptive pain,
(e) neuropathic pain, including painful diabetic neuropathy, pain associated with post-herpetic neuralgia, or trigeminal neuralgia and HIV-related neuropathy, large fiber neuropathy including atrophy
(f) hyperalgesia,
(g) allodynia,
(h) central pain, central post-stroke pain, pain resulting from multiple sclerosis, pain resulting from spinal cord injury, or pain resulting from Parkinson's disease or epilepsy,
(i) cancer pain,
(j) post-operative pain,
(k) visceral pain, including digestive visceral pain and non-digestive visceral pain, pain due to gastrointestinal (GI) disorders, pain resulting from functional bowel disorders (FBD), pain resulting from inflammatory bowel diseases (IBD), pain resulting from dysmenorrhea, pelvic pain, cystitis, interstitial cystitis or pancreatitis,
(l) musculo-skeletal pain, myalgia, fibromyalgia, spondylitis, sero-negative (non-rheumatoid) arthropathies, non-articular rheumatism, dystrophinopathy, Glycogenolysis, polymyositis, pyomyositis,
(m) heart or vascular pain, pain due to angina, myocardical infarction, mitral stenosis, pericarditis, Raynaud's phenomenon, scleredoma, or skeletal muscle ischemia,
(n) head pain including migraine, migraine with aura, migraine without aura, cluster headache, tension-type headache.
(o) orofacial pain, including dental pain, temporomandibular myofascial pain or tinnitus, or
(p) back pain, bursitis, menstrual pain, referred pain, trigeminal neuralgia, hypersensitisation, pain resulting from spinal trauma and/or degeneration or stroke,
(q) fibromyalgia Treatment of pain includes, but is not limited to, preventing, ameliorating, controlling, reducing incidence of, or delaying the development or progression of pain According to another aspect of the invention there is provided the p75NTR(NBP)-Fc fusion protein as described herein or the preferred embodiments thereof, or the nucleic acid molecule or vector as described herein wherein the p75NTR(NBP)-Fc fusion protein or the nucleic acid molecule or vector is for separate, sequential or simultaneous use in combination with a second or more pharmacologically active compound or compounds. Preferably the second or more pharmacologically active compound or compounds of the combination may include but is not limited to;

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis (trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl thio]-5-chloro-3-pyridinecarbonitrile; 24[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile. N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);
a sodium channel blocker, such as lidocaine; or
a 5-HT3 antagonist, such as ondansetron;
and the pharmaceutically acceptable salts and solvates thereof.

According to a further aspect of the present invention there is provided a method of treating, preventing, ameliorating, controlling, reducing incidence of, or delaying the development or progression of pain in an individual, comprising administration to the individual of an effective amount of the p75NTR(NBP)-Fc fusion protein as described herein, or the preferred embodiments thereof, or the nucleic acid molecule or vector as described herein.

The present invention is applicable in both human and veterinary medical fields. Preferably the individual is a mammal, for example a companion animal such as a horse, cat or dog or a farm animal such as a sheep, cow or pig. Most preferably the individual is a human.

According to a further aspect of the present invention there is provided a pharmaceutical composition for any one or more of treating, preventing, ameliorating, controlling, reducing incidence of, or delaying the development or progression of pain comprising the p75NTR(NBP)-Fc fusion protein as described herein, or the preferred embodiments thereof, or the nucleic acid molecule or vector as described herein and a pharmaceutically acceptable carrier and/or an excipient.

Preferably the p75NTR(NBP)-Fc fusion protein as described herein, or the preferred embodiments thereof, or the nucleic acid molecule or vector as described herein or the pharmaceutical composition as described herein is prepared for or suitable for oral, sublingual, buccal, topical, rectal, inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local or epicutaneous administration.

Most preferably the p75NTR(NBP)-Fc fusion protein as described herein, or the preferred embodiments thereof, or the nucleic acid molecule or vector as described herein be administered directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Preferably the p75NTR(NBP)-Fc fusion protein as described herein, or the preferred embodiments thereof, or the nucleic acid molecule or vector as described herein or the pharmaceutical composition as described herein is prepared for or suitable for administration prior to and/or during and/or after the onset of pain or for such use.

Preferably the p75NTR(NBP)-Fc as described herein, or the preferred embodiments thereof, or the nucleic acid molecule or vector as described herein or the pharmaceutical composition as described herein is for or prepared for administration between once to 7 times per week, further preferably between once to four times per month, further preferably between once to six times per 6 month period, further preferably once to twelve times per year. Preferably the medicament is to be or prepared to be peripherally administered in a period including but not limited to: once daily, once every two, three, four, five or six days, weekly, once every two weeks, once every three weeks, monthly, once every two months, once every three months, once every four months, once every five months, once every six months, once every seven months, once every eight months, once every nine months, once every ten months, once every eleven months or yearly.

Preferably the p75NTR(NBP)-Fc fusion protein as described herein, or the preferred embodiments thereof, or the nucleic acid molecule or vector as described herein or the pharmaceutical composition as described herein is for or is prepared for administration at a concentration of between about 0.05 to about 200 mg/ml; preferably at any one of about 0.05, 0.1, 0.5, 1, 5, 10, 15, 20, 25, 30, 35, 40, 45, 50, 55, 60, 65, 70, 75, 80, 85, 90, 95, 100, 110, 120, 130, 140, 150, 160, 170, 180, 190 or 200 mg/ml+/−about 10% error, most preferably at about 3 mg/ml in veterinary applications and 0.1 in humans.

Preferably the p75NTR(NBP)-Fc fusion protein as described herein, or the preferred embodiments thereof, or the nucleic acid molecule or vector as described herein or the pharmaceutical composition as described herein is for or is prepared for administration at a concentration of between about 0.1 to about 200 mg/kg of body weight; preferably at any one of about 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190 or about 200 mg/kg of body weight+/−about 10% error, most preferably at about 10 mg/kg in veterinary applications and 0.3 in humans According to yet another aspect of the present invention there is provided the p75NTR(NBP)-Fc fusion protein as described herein or the preferred embodiments thereof, or the nucleic acid molecule or vector as described herein or the pharmaceutical composition as described herein for use in any one or more of the prevention or treatment or for ameliorating, controlling, reducing incidence of, or delaying the development or progression of a condition or the symptoms of a condition associated with any one or more of the neurotrophins NGF, BDNF, NT-3, NT-4/5.

NGF (Nerve growth factor) binds with at least two classes of receptors: the p75NTR and TrkA, a transmembrane tyrosine kinase, it is involved in axonal growth, branching and elongation. Conditions and symptoms associated with NGF are known. NGF is expressed in and associated with inflammatory conditions and pain [Protein Sequence NP_002497.2, NP_038637]. Also, NGF has been shown to play a role in number cardiovascular diseases, such as coronary atherosclerosis, obesity, type 2 diabetes, and metabolic syndrome as well as in Multiple Sclerosis. Reduced plasma levels of NGF (and also of BDNF) have been associated with acute coronary syndromes and metabolic syndromes. NGF is also related to various psychiatric disorders, such as dementia, depression, schizophrenia, autism, Rett syndrome, anorexia nervosa, and bulimia nervosa and has also been implicated in development of Alzheimer's disease and neurodegenerative disorders. NGF has also been shown to accelerate wound healing and there is evidence that it could be useful in the treatment of skin ulcers and corneal ulcers, it has been shown to reduce neural degeneration and to promote peripheral nerve regeneration in rats.

BDNF (brain-derived neurotrophic factor) is a neurotrophin which supports neuronal survival and growth during development of the nervous system [Protein Sequence NP_001137277.1, NP_001041604]. BDNF binds cell surface receptors TrkB and p75NTR and also modulates the activity of Alpha-7 nicotinic receptor. Conditions and symptoms associated with BDNF are known. BDNF has been shown to play a significant role in the transmission of physiologic and pathologic pain, particularly in models of acute pain, inflammatory pain and neuropathic pain, where BDNF synthesis is found to be greatly increased; also BDNF has been shown to be up-regulated in conditions of chronic pain as well as further conditions such as eczema and psoriasis. Downregulation of BDNF is seen in depression, schizophrenia, obsessive-compulsive disorder, Alzheimer's disease, Huntington's disease, Rett syndrome, and dementia, as well as anorexia nervosa and bulimia nervosa.

Neurotrophin-4 (NT-4), also known as neurotrophin-5 (NT-5), is a neurotrophic factor that signals predominantly through the p75NTR and TrkB receptors and promotes the survival of peripheral sensory sympathetic neurons. The mature peptide of this protein is identical in all mammals examined including human, pig, rat and mouse. [Protein Sequence NP_006170, NP_937833]. NT-4 is synthesized by most neurons of the dorsal root ganglion (DRG) and those in the paravertebral and prevertebral sympathetic ganglia, spinal dorsal and ventral horn and is found expressed in many tissues including the prostate, thymus, placenta and skeletal muscle. Conditions and symptoms associated with NT-4/5 are known. Defects in NT4/5 are associated with susceptibility to primary open angle glaucoma. Neurotrophin 4 has also been shown to contribute to breast cancer cell survival and is a target to inhibit tumour growth. NT-4/5 is known to be involved in pain-signalling systems such as nociceptive pain, upregulation of NT-4/5 is also seen in chronic inflammatory conditions of the skin, such as dermatitis, eczema, prurigo lesions of atopic dermatitis. Down regulation of NT-4/5 is seen in Alzheimer's Disease, Huntington's disease.

Neurotrophin-3 (NT-3), is a neurotrophin that is structurally related to beta-NGF, BDNF, and NT-4, and that controls survival and differentiation of mammalian neurons and the maintenance of the adult nervous system, and may affect development of neurons in the embryo when it is expressed in human placenta. Conditions and symptoms associated with NT3 are known. NTF3-deficient mice generated by gene targeting display severe movement defects of the limbs. NT-3 signals through the Trk receptors and promotes the growth and survival of nerve and glial cells[Protein Sequence NP_001096124.1 and NP_0327681. The amino acid sequences of human, Mouse and rat NT-3 are identical. NT3 and its cognate receptor, tyrosine kinase C (TrkC), are known to modulate neuropathic pain and nociceptive pain and the mechanism of nociception and proporioception, for example NT3 expression is increased in the small DRG cells of neuropathic animals. NT3 expression is also associated with neuropathies such as diabetic polyneuropathy and HIV-related neuropathy, large fiber neuropathy including atrophy, it is further involved in the development of hyperalgesia (a decrease in the threshold of a normally noxious stimuli), allodynia (a non-noxious stimulus becomes noxious), and spontaneous pain (pain in the apparent absence stimuli) and is a known modulator of muscle pain.

Accordingly in a further embodiment provides p75NTR neurotrophin binding protein NBP)-Fc fusion protein, comprising or consisting of the amino acid sequence set forth SEQ ID NO. 1 for use in treating:
 a. skin conditions such as eczema, psoriasis, dermatitis, prurigo lesions of atopic dermatitis
 b. psychiatric conditions such as obsessive-compulsive disorder, depression, schizophrenia, anorexia nervosa, bulimia nervosa,
 c. cardiovascular diseases, such as coronary atherosclerosis, acute coronary syndromes, obesity, type 2 diabetes, and metabolic syndrome,
 d. multiple sclerosis
 e. healing and repair, such as accelerating wound healing, treatment of skin ulcers and corneal ulcers,
 f. neurodegeneration, neurodevelopmental or neurological conditions such as Huntington's disease, Rett syndrome, dementia, Alzheimer's disease, autism, development neurodegenerative disorders, primary open angle glaucoma, to reduce neural degeneration and to promote peripheral nerve regeneration.
 g. cancer, particularly breast cancer,
 h. rheumatoid arthritis, and osteoarthritis
 i. cystitis, endometriosis The invention will now be described by reference to the following examples which are provided to illustrate, but not to limit, the invention.

EXAMPLES

Process for Making Truncated p75NTR-Fc Molecule (SEQ ID NO. 1)

A single gene GS vector (using Lonza's GS Xceed™ Gene Expression System) was established. The product was progressed to transient transfections in Chinese Hamster Ovary cells (CHOK1SV GS-KO) using the single gene vector (SGV) to express the product.

Linearised SGV was transfected into CHOK1SV GS-KO cells and cultured under selection conditions as stable pooled cultures. The propagated stable pools were expanded to 10 L culture volume and subjected to an abridged fed batch overgrow with 2 bolus feeds on day 4 and 8. Cultures were harvested on day 11 and supernatant titre determined by Protein A HPLC. Clarified supernatant for Protein A purification was obtained by centrifugation followed by filter sterilisation using a 0.22 μm filter cartridge. The clarified supernatant was concentrated approximately 2.5-fold using tangential flow filtration. Protein A purification was performed using clarified concentrated supernatant equivalent to 1 g of product based on Protein A HPLC data. Product quality analysis in the form of SE-HPLC, SDS-PAGE, IEF and endotoxin detection was carried out using purified material at 1 mg/ml.

Affinity of Truncated p75NTR-Fc Molecule (SEQ ID NO. 1) for Individual neurotrophins A Biacore chip was prepared in an experiment in which Protein A was amine coupled to flow cells 1 and 2. Single cycle kinetics of NGF binding to captured p75-Fc were measured.

The binding capacity ($R_{max}$) of a chip surface depends of the immobilised level of the ligand (fusion protein). For a kinetics study an $R_{max}$ of 50-100 RU is advised. By using the molecular weights of the p75-Fc and NGF, a desired immobilisation level for the fusion protein can be calculated.

$R_{max}$=(NGF molecular weight/fusion protein molecular weight)×immobilisation level×stoichiometric ratio: 50=(13,500/87,000)×immobilisation level×1.

Hence, the immobilisation level required=(87,000/13,500)×50=322 RU Sequence 1 (SEQ ID NO. 1) were immobilised onto the Protein A chip prior to single cycle kinetics.

Using a manual run, Truncated p75-Fc (SEQ ID NO. 1) was captured onto flow cell 2 of the Protein A chip until the desired level of approx. 380 RU was achieved. This was performed with a 22 second injection at a flow rate of 10 µl/min and Truncated p75-Fc (SEQ ID NO. 1) concentration 10 µg/ml which resulted in 418 RU of the fusion protein captured onto the protein A surface.

In the first instance NGF concentrations of 10, 5 2.5, 1.25 and 0.625 nM were tested. These concentrations were tested as the $K_D$ for the fusion protein was approximated to be within this range of NGF concentrations.

The single cycle kinetics method involved:
injecting 0.625 nM of NGF onto the captured p75-Fc for 120 seconds at 30 µl/min
this process was then repeated with an injection of NGF at 1.25 nM, followed by 2.5, 5 and 10 nM
after the final concentration of NGF had been injected a 600 second dissociation phase was performed by flowing the running buffer (HBS-EP) over the chip.

Once completed the chip was regenerated back to its Protein A surface by injecting 10 mM Glycine HCl, pH 2 for 60 seconds at 30 µl/min.

Sequence 1 (SEQ ID NO. 1) p75-Fc was then captured onto the chip by performing a 38 second injection at a flow rate of 10 µl/min at a concentration of 10 µg/ml. This achieved the desired level of 430 RU. The single cycle kinetics procedure described above was then repeated.

Data Analysis

The fusion protein-NGF binding data was analysed in the following manner using the Biacore™ T200 evaluation software v1:

Data is recorded for the binding of NGF to the fusion protein on flow cell 2 (Fc=2) and for NGF flowing over the control flow cell 1 (Fc=1; protein A alone).

The data from Fc=1 is then subtracted from Fc=2 to give "2-1" binding data.

The 2-1 binding data for an injection of 0 nM (HBS-EP running buffer alone) is then subtracted from all the 2-1 binding data to control for any drifts in baseline throughout the experiment.

Finally, this data is then fitted to a 1:1 binding model to calculate binding characteristics including association rates (ka), dissociation rates (kd) and affinities ($K_D$).

This process was repeated for BDNF, NT-3 and NT-4. The results are shown in Table 1 and FIG. 1).

TABLE 1

Biacore ™ Affinity of Sequences 1 and 3 for each neurotrophin

| Sequence | NT-3 (pM) | NT-4 (pM) | BDNF (pM) | NGF (pM) |
| --- | --- | --- | --- | --- |
| 1 | 20 | 100 | 50 | 500 |
| 3 (Reference) | 14 | 181 | 48 | 525 |

This experiment confirms that SEQ ID NO. 1 maintains similar affinity with neurotrophins despite the removal of the stalk region (SEQ ID NO. 4) when compared to SEQ ID NO. 3, which corresponds to the amino acid sequence of the p75NTR(NBP)-Fc fusion (SEQ ID NO. 1) including the stalk region of SEQ ID NO. 4.

Determination of the Potency of p75NTR-Fc to Inhibit the Neurotrophin-Induced Activation of Trk Receptors The potency of Truncated p75NTR-Fc to inhibit the neurotrophin-induced response in cells expressing TrkA, TrkB or TrkC receptors was determined using DiscoverX AbHunter kits (TrkA [93-0462E3FS], TrkB [93-0463E3FS], TrkC [93-0464E3BCP16]).

Briefly, frozen cells were thawed and plated in 96-well microplates at a density of 10,000 cells/well. Following an 18-hour incubation at 37° C., 5% $CO_2$, the assay was performed. For cells expressing TrkA receptors, a concentration-effect curve to nerve growth factor (NGF) was included in each plate. Increasing concentrations of Truncated p75NTR-Fc(SEQ ID NO. 1) preincubated for 1 hour with an EC80 concentration of NGF to ensure equilibration, were added to appropriate wells to produce inhibition curves, and potency was measured by the IC50 value. The same experimental design was used for cells expressing TrkB and TrkC receptors, except the neurotrophins used to induce receptor activation were brain-derived neurotrophic factor (BDNF) or neurotrophin-4 (NT-4) for TrkB and neurotrophin-3 (NT-3) for TrkC receptors.

Following addition of buffer, neurotrophin or Truncated p75NTR-Fc/neurotrophin the plates were incubated for 3 hours at room temperature. Detection reagent was then added as per kit instructions and the plates incubated at room temperature for 2 hours. The luminescence signal was measured using a luminescence plate reader.

Data were expressed as Relative Light Units (RLUs) and as a proportion of the RLU measured from wells containing the highest concentration of neurotrophin. Unconstrained concentration effect curves were fitted by non-linear, 4 parameter, logistical regression analysis. The neurotrophin $EC_{50}$ value was estimated from the agonist curve and used as a measure of inter-assay variability. The $IC_{50}$, $E_{max}$ and slope values of the antagonists were estimated from the inhibition curves. The data is shown in Table 2.

TABLE 2

Inhibition of neurotrophin/Trk signaling by Truncated p75NTR-Fc

|  | NGF-induced activation of TrkA | BDNF-induced activation of TrkB | NT-3-induced activation of TrkC | NT-4-induced activation of TrkB |
| --- | --- | --- | --- | --- |
| $EC_{50}$ | 0.23 nM | 0.7 nM | 0.1 nM | 12 pM |
| SEQ ID NO. 1 | $IC_{50}$ 1.5 nM | $IC_{50}$ No inhibition | $IC_{50}$ 0.5 nM | $IC_{50}$ 1 nM |

This experiment confirms that SEQ ID NO. 1 maintains the ability to interact with neurotrophins in an in vitro environment despite the removal of the stalk region (SEQ ID NO. 4). The molecule therefore shows promise as a treatment for neurotrophin-mediated conditions, in particular pain.

Characterisation of Isoelectric Point

The highly glycosylated molecule of SEQ ID NO. 3 as a theoretical iso-electric point of 4.5. However, as observed in FIG. 1 the protein has a number of indistinct bands on a IEF gel ranging from 3.4 to 4.2 (significantly lower than the theoretical iso-electric point of the protein). This property of the molecule provides a number of disadvantages ranging from manufacture, formulation, identification of the molecule, batch to batch variation, immunogenicity and pharmacokinetics.

Removing the highly glycosylated stalk region of SEQ ID NO. 3 provides a more predictable molecule (SEQ ID NO. 1). The iso-electric point of SEQ ID NO. 1 predicted to be 4.6. As demonstrated in FIG. 2, the observed iso-electric point is very similar to that of the theoretical iso-electric point. This enables SEQ ID NO. 1 to have a superior manufacturability profile, improved protein identification, greater range possible formulations, reduced immunogenicity potential and improved pharmacokinetic profile.

Efficacy in Pain Model

The molecule of the present invention was tested in an animal model of analgesia.

Adult male Wistar rats were allowed to acclimatise for one week. Animals were familiarised with the testing apparatus during the habituation week. On Day 0, animals were administered with 150 microliters of complete Freund's adjuvant (CFA) by subcutaneous injection close to the right tibio-tarsal joint. Treatments were given according to the administration schedule below. Paw withdrawal thresholds to a mechanical stimulus were determined using the von Frey test on Day −1 (pre-CFA values), on Day 5 (post-CFA and pretreatment values) and on Day 10 and Day 12 (post-CFA and post-treatment values). Animals were randomised into experimental groups of 10 animals based on the paw withdrawal threshold values calculated on Day 5. On Day 12, blood samples were collected under terminal anaesthesia into lithium heparincoated tubes and processed to isolate plasma for pharmacokinetic analysis. Plasma samples were stored at −20° C.

On day 6 one group was given an intra-peritoneal injection of molecule of the present invention in Phosphate Buffered Saline (PBS), the other group an injection of IgG1 Fc in PBS (vehicle)

Administration volume for intra-peritoneal injection was 1 ml/kg. Molecule of present invention was administered at 3 mg/kg.

Efficacy was measured using the von Frey Test. On Day −1, Day 5, Day 10 and Day 12, paw withdrawal thresholds to a mechanical stimulation were calculated to establish pre-CFA, post-CFA and post-treatment values. Animals were placed unrestrained in a Perspex enclosure and on a mesh floor. The plantar surface of the right hind paws was stimulated using calibrated von Frey filaments following the up-and-down method. A paw withdrawal threshold, expressed in grams, was calculated for each animal.

Complete Freund's adjuvant administration induced a highly significant decrease of the paw withdrawal thresholds in the vehicle-treated group on Day 5, Day 10 and Day 12 when compared to Day 0 ($p<0.0001$).

The molecule of the present invention, administered at 3 mg/kg, induced a significant increase of the paw withdrawal thresholds when compared to the vehicle-treated group on Day 10 ($p<0.05$) and Day 12 ($p<0.01$).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A p75NTR neurotrophin binding protein (NBP)-Fc fusion protein, comprising the amino acid sequence set forth by SEQ ID NO: 1.

2. The p75NTR(NBP)-Fc fusion protein according to claim 1 wherein the p75NTR(NBP) binds to any of NGF, BDNF, NT3 or NT4/5 with a binding affinity (Kd) of between about 1 pM to about 100 nM as measured by surface plasmon resonance at 20° C.

3. The p75NTR(NBP)-Fc fusion protein according to claim 1, for use in therapy.

4. The p75NTR(NBP)-Fc fusion protein according to claim 1, for use in the treatment of pain.

5. A pharmaceutical composition comprising a p75NTR neurotrophin binding protein (NBP)-Fc fusion protein comprising the amino acid sequence set forth by SEQ ID NO: 1, and a pharmaceutically acceptable diluent or carrier.

6. A method of treating pain in an individual in need thereof comprising administering to said individual a composition comprising a therapeutically effective amount of the p75NTR(NBP)-Fc fusion protein according to claim 1, thereby ameliorating the pain.

7. The method of claim 6, wherein the composition further comprises a pharmaceutically acceptable carrier.

* * * * *

SEQUENCE LISTING

```
<160> NUMBER OF SEQ ID NOS: 4

<210> SEQ ID NO 1
<211> LENGTH: 399
<212> TYPE: PRT
<213> ORGANISM: Artificial Sequence
<220> FEATURE:
<223> OTHER INFORMATION: Fusion Protein

<400> SEQUENCE: 1

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
```

```
                130                 135                 140
Thr Glu Arg Gln Leu Arg Glu Cys Thr Arg Trp Ala Asp Ala Glu Cys
145                 150                 155                 160

Glu Glu Ile Pro Gly Gly Gly Glu Pro Lys Ser Ser Asp Lys Thr
                165                 170                 175

His Thr Cys Pro Pro Cys Pro Ala Pro Glu Leu Leu Gly Gly Pro Ser
                180                 185                 190

Val Phe Leu Phe Pro Pro Lys Pro Lys Asp Thr Leu Met Ile Ser Arg
                195                 200                 205

Thr Pro Glu Val Thr Cys Val Val Val Asp Val Ser His Glu Asp Pro
210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
                260                 265                 270

Lys Cys Lys Val Ser Asn Lys Ala Leu Pro Ala Pro Ile Glu Lys Thr
275                 280                 285

Ile Ser Lys Ala Lys Gly Gln Pro Arg Glu Pro Gln Val Tyr Thr Leu
                290                 295                 300

Pro Pro Ser Arg Asp Glu Leu Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
                340                 345                 350

Ser Asp Gly Ser Phe Phe Leu Tyr Ser Lys Leu Thr Val Asp Lys Ser
                355                 360                 365

Arg Trp Gln Gln Gly Asn Val Phe Ser Cys Ser Val Met His Glu Ala
                370                 375                 380

Leu His Asn His Tyr Thr Gln Lys Ser Leu Ser Leu Ser Pro Gly
385                 390                 395

<210> SEQ ID NO 2
<211> LENGTH: 19
<212> TYPE: PRT
<213> ORGANISM: Artificial Sequence
<220> FEATURE:
<223> OTHER INFORMATION: Leader Sequence

<400> SEQUENCE: 2

Met Glu Trp Ser Trp Val Phe Leu Phe Phe Leu Ser Val Thr Thr Gly
1               5                   10                  15

Val His Ser

<210> SEQ ID NO 3
<211> LENGTH: 443
<212> TYPE: PRT
<213> ORGANISM: Artificial Sequence
<220> FEATURE:
<223> OTHER INFORMATION: Fusion protein including stalk region

<400> SEQUENCE: 3

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
```

```
            20                  25                  30
Gln Thr Val Cys Glu Pro Cys Leu Asp Ser Val Thr Phe Ser Asp Val
            35                  40                  45

Val Ser Ala Thr Glu Pro Cys Lys Pro Cys Thr Glu Cys Val Gly Leu
        50                  55                  60

Gln Ser Met Ser Ala Pro Cys Val Glu Ala Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
                100                 105                 110

Lys Gln Asn Thr Val Cys Glu Glu Cys Pro Asp Gly Thr Tyr Ser Asp
            115                 120                 125

Glu Ala Asn His Val Asp Pro Cys Leu Pro Cys Thr Val Cys Glu Asp
            130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
                180                 185                 190

Gln Asp Leu Ile Ala Ser Thr Val Ala Gly Val Val Thr Thr Val Met
                195                 200                 205

Gly Gly Gly Gly Glu Pro Lys Ser Ser Asp Lys Thr His Thr Cys Pro
            210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly
            435                 440
```

```
<210> SEQ ID NO 4
<211> LENGTH: 43
<212> TYPE: PRT
<213> ORGANISM: Artificial Sequence
<220> FEATURE:
<223> OTHER INFORMATION: Stalk region

<400> SEQUENCE: 4

Arg Trp Ile Thr Arg Ser Thr Pro Pro Glu Gly Ser Asp Ser Thr Ala
1               5                   10                  15

Pro Ser Thr Gln Glu Pro Glu Ala Pro Pro Glu Gln Asp Leu Ile Ala
            20                  25                  30

Ser Thr Val Ala Gly Val Val Thr Thr Val Met
            35                  40
```